United States Patent [19]
Petrila et al.

[11] Patent Number: 5,817,929
[45] Date of Patent: Oct. 6, 1998

[54] VISCOSITY MONITORING SYSTEM

[75] Inventors: Steven C. Petrila, Crete; Scott P. Gossett, Tinley Park; Robert F. Lantz, III, Crete, all of Ill.

[73] Assignee: The Ringwood Company, Chicago, Ill.

[21] Appl. No.: 721,802

[22] Filed: Sep. 27, 1996

[51] Int. Cl.⁶ .................................................. G01N 11/00
[52] U.S. Cl. ........................................ 73/54.01; 106/206.1
[58] Field of Search ............................. 106/206.1, 214.2, 106/213.1; 366/297, 295; 73/54.01, 64.56, 864.81, 864.83

[56] References Cited

U.S. PATENT DOCUMENTS

| | | | |
|---|---|---|---|
| 3,836,376 | 9/1974 | Hampton et al. | 106/214.02 |
| 4,544,489 | 10/1985 | Campbell et al. | 210/709 |
| 4,683,837 | 8/1987 | Linke et al. | 118/612 |
| 5,046,856 | 9/1991 | McIntire et al. | 366/291 |
| 5,087,471 | 2/1992 | Combes et al. | 426/573 |
| 5,135,310 | 8/1992 | Nodus et al. | 366/297 |
| 5,358,559 | 10/1994 | Fitt et al. | 106/213 |

*Primary Examiner*—Hezron E. Williams
*Assistant Examiner*—Jay L. Politzer
*Attorney, Agent, or Firm*—Laff, Whitesel, Conte & Saret, Ltd.

[57] ABSTRACT

A corrugator paste or adhesive manufacturing system provides a viscosity testing tank which is separate from other tanks used in the system. Separate storage tanks are provided for storing each of a plurality of different pastes or adhesives. A closed loop system or network of pipes circulates paste or adhesive from a mixing tank or tanks and from each of the storage tanks through a viscosity monitoring station, and then back to the storage tanks after a viscosity test is performed in the testing tank. An electronic control circuit allocates a time for giving each tank access to the viscosity monitoring station and for comparing the measurements during each such time with a pre-stored criterion for the paste or adhesive that is then being measured. If the viscosity read at the monitoring station corresponds to the stored criterion, the adhesive is returned to its proper storage tank. If there is no such correspondence, various controls may be automatically operated to correct the composition of the paste or adhesive. If the viscosity reading indicates that the adhesive is hopeless, suitable valves are operated to dump an entire batch of said adhesive.

16 Claims, 2 Drawing Sheets

VISCOSITY MONITORING SYSTEM

This invention relates to viscosity monitoring systems and more particularly—but not exclusively—to means for monitoring the viscosity of paste or adhesive used in a corrugated cardboard manufacturing machine.

Corrugated cardboard manufacturing machines use paste or adhesives for a number of different operations, such as gluing facing board onto corrugated flutes. There are different specifications for different places where paste or adhesive is used. For example, an adhesive having one specification is often used for single face board where the facing board is glued to crests of flutes on only one side of the corrugations. If a double face board has a second facing board glued to the crests on the other side of the flutes, an adhesive with a different specification may be used.

Those who are skilled in the art will readily recognize how the corrugation machine may use essentially similar paste or adhesive, but with many different specifications. These specifications relate to different parameters, such as the heat required, the gel point, etc. Most of the specifications can be monitored by monitoring the viscosity of the paste or adhesive. Therefore, it is very important for the manufacturer of the paste or adhesive to be able to keep a fairly close real time reading of viscosity and to automatically adjust production to maintain fixed parameters responsive to such readings.

The conventional practice is to place a viscosity reading meter ("viscometer") in a mixing stage where the paste or adhesive ingredients first come together. However, this practice leads to many problems. Sometimes the ingredients have not been thoroughly mixed at the time of the meter reading. If the viscometer is immersed in an almost pure liquid or in almost pure solid parts of the insufficiently mixed paste or adhesive, the reading could show a higher or lower, when in fact, the paste or adhesive would be nearly perfect if the reading is taken after complete mixing. This early viscosity reading could lead to an introduction of too much water or solids to adjust the current formular viscosity.

Likewise, paste or adhesive is subject to aging. A mixture which has perfect viscosity at the time of mixing may swell while in storage and become too viscous. Those skilled in the art will readily perceive other reasons for false readings.

Another problem which is often encountered is that the paste or adhesive may be left in the mixer too long a period of time so that it crystallizes on the viscometer. The mixer may be easy to clean; however, the viscosity meter usually is much more difficult to clean.

Still another problem is that the corrugation industry has its own way of measuring viscosity which is not widely used by other industries. More particularly, the viscosity measurements use in the corrugation industry are known as the Stein-Hall viscosity scale. To take a Stein-Hall reading, a fixed amount of the material under test is caused to pass through or leak out an aperture of known diameter. A numerical reading, which is the Stein-Hall index, is produced by measuring the amount of time required for the material to leak through the aperture. Thus, any viscometer used in a corrugated cardboard plant must give readings on the Stein-Hall scale.

Accordingly, an object of the invention is to provide a method of automatically measuring the viscosity/flow properties and the temperature of starch paste or adhesive. Here, an object is to directly relate the viscosity/flow property numbers to the corrugated industries' standard "Stein-Hall" viscosity numbers.

A more particular object is to integrate viscosity monitoring at three or more distinct work stations in a corrugated cardboard installation as follows: (1) monitoring of paste or adhesive in storage tanks, intermediate tanks, and mixing tanks; (2) giving test results on the Stein-Hall viscosity scale to set automatic machinery which makes a starch paste or adhesive; and (3) monitoring the corrugator sump, run tanks, and use tanks.

In keeping with an aspect of the invention, these and other objects are accomplished by providing separate storage tanks for each of a plurality of different pastes or adhesives (normally any number from 1 to 7 tanks.) A closed loop system circulates paste or adhesive from a mixing tank and each of the storage tanks through a viscosity monitoring station and back to the appropriate storage tanks. An electronic control circuit allocates time frames for giving each tank access to the viscosity monitoring station and for comparing the measurements during each such time frame with a pre-stored criterion for the paste or adhesive that is then being measured. If the viscosity read at the monitoring station corresponds to the stored criterion, the paste or adhesive is returned to its proper storage tank. If there is no such correspondence, hopefully the various controls are automatically operated to correct the adhesive and to bring it into specification. If the viscosity reading indicates that the adhesive is hopeless, suitable valves are operated to dump an entire batch.

Preferred embodiments of the invention are shown in the attached drawings, in which.

Figure 1:
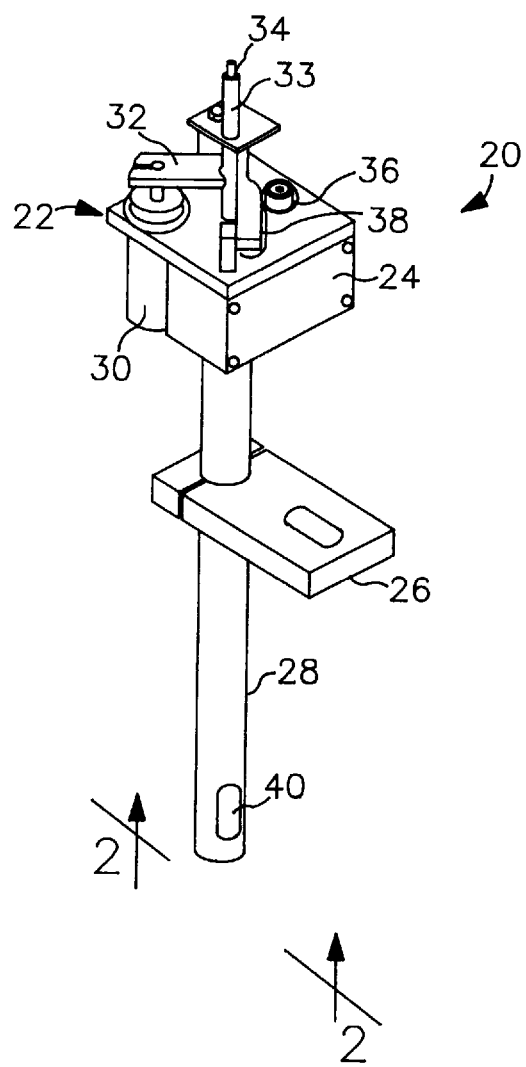
FIG. 1 is a perspective view of a known viscometer that is used in the inventive system.

A viscometer 20 (FIG. 1) includes a lifting mechanism 22, a timing switch 24, a mounting bracket 26, and a measuring tube 28. The mounting bracket 26 is simply a metal plate which may be bolted or otherwise clamped to any suitable structure (not shown in FIG. 1).

The lifting mechanism includes an air cylinder 30 which raises or lowers a lifter plate 32. The lifter plate is rigidly attached to a rod 33 slidingly mounted in the measuring tube 28; hence, the air cylinder raises and lowers the rod 33 which slides within measuring tube. Rod 33 is attached to a bushing and cap 42 (FIG. 2) which has a bore that is almost completely filled by stationary piston 40 when the bushing and cap 42 is in its lowermost position. A level 36 facilitates adjustments of the viscometer's vertical position. A suitable sensor or switch arm 38 determines when the rod 33 is first lowered and then raised to the correct levels.

The viscometer that was used in a system that was actually built is available from the Norcross Corporation at 255 Newtonville Avenue, Newton, Mass. 02158. Other sources of suitable viscometers are PAD Systems & Technology, Montreal, Canada and Cambridge Applied Systems, 57 Smith Place, Cambridge, Mass. 02138.

In operation, the adhesive to be measured fills a tank containing the viscometer. Then, the viscometer starts a process for testing the paste or adhesive. First, the viscometer takes in a sample of the product by filling a small chamber 40 with adhesive when rod 33 lifts bushing and cap 42 and adhesive fills the space provided by a bore in cap 42 shown in FIG. 2 as being occupied by piston 44. Then, bushing and cap 42 is released so that it falls of its own weight over piston 44, thereby forcing the adhesive inside the bore of cap 42 to leave via the clearance space 45 between the bore and piston 44. A limit switch 38 signals the start/end of the fall.

Since there is only a small clearance space 45 between the bore in cap 42 and piston 44, an extended time period is required for the adhesive to evacuate the chamber as the bushing and cap 42 settles to the bottom of its travel. The timer 24 initiates a timing cycle upon the start of the fall of cap and bushing 42 and ends upon the completion of the fall. The time required for the fall is measured at a rate of 1/100th second. This timing of an cycle is then converted to a number on the "Stein-Hall" viscosity scale by an associated programmable controller.

Figure 2:
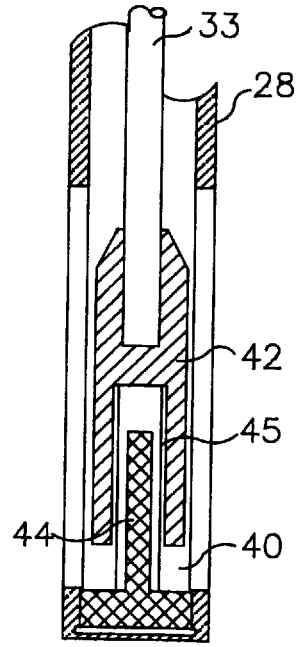
FIG. 2 is an enlarged cross-section taken along line 2—2 of FIG. 1 showing the measuring device used in the viscometer.
Figure 3:
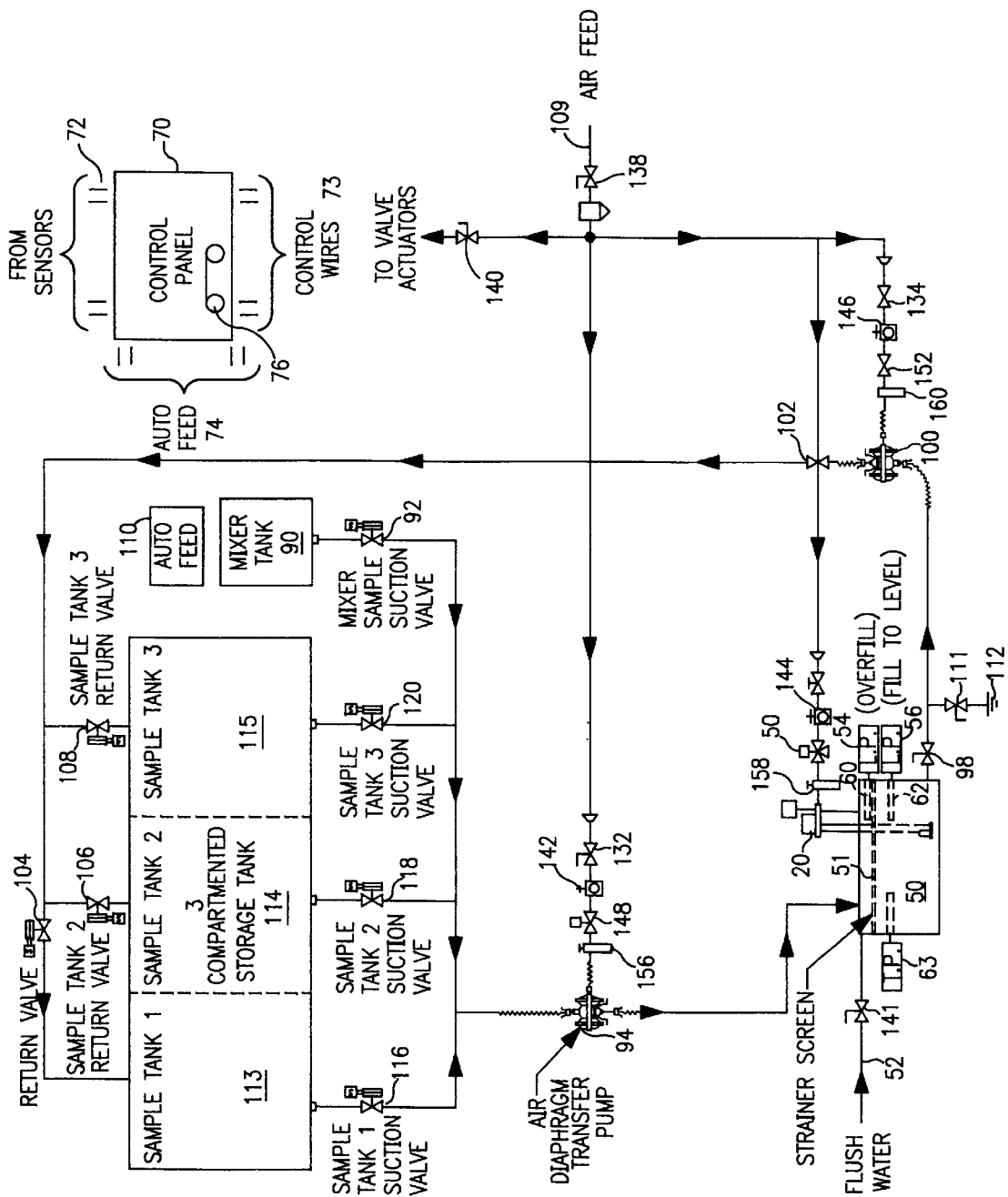
FIG. 3 is a schematic showing of a paste or adhesive monitoring system incorporating the invention.

FIG. 3 shows the inventive system which is controlled by a viscometer for mixing paste or adhesive. The viscometer 20 of FIGS. 1 and 2 is mounted in a testing tank 50 which receives adhesive via a pipe 52. An inlet straining screen 51 is included in the testing tank 50 to filter out any paper scraps or gelled starch that might otherwise foul the system. Flush water is provided to the testing tank via pipe 52 in order to assist in a clean-up cycle during shut down of the system. The tank 50 is constructed with a pitched bottom and a half drain cut into the lowest point of the tank to allow for complete evacuation in order to minimize adhesive contamination.

The level of paste or adhesive is maintained by upper and lower level sensors 54, 56 coupled to probes 60, 62. The testing tank 50 itself is fitted with two level probes 60, 62 for sensing the amount of adhesive in the tank. One probe 62 is used to sense a fill-to-level and the other probe 60 is used as a safety device to sense an overfill condition. While any suitable level sensor may be used, one system that was actually constructed used sensors where an RF signal was sent into the testing tank 50. The high and low level probes receive the RF signal if they are not submerged in paste or adhesive. If they are submerged, they do not receive the RF signal. The tank also has a temperature probe 63 of any suitable design. The temperature must be monitored in the testing tank 50 due to the temperature sensitive nature of the adhesive sample which becomes thicker as it gets colder and thinner as it gets hotter.

The system of FIG. 3 is operated under the control of a control panel 70. The level of adhesive sensed at 60, 62 and the temperature sensed at 63 produce electrical signals that are sent to the control panel 70 via wires 72. Suitable control signals are sent out from the control panel via wires 73 in order to control the operation of the system and via wires 74 to make suitable adjustments, as they are required. The control panel sends its control signals via wires 73 which lead to various valves, pumps and the like, and via wires 74 to control the feeding of the ingredients into the system in order to make the paste or adhesive.

A chart or strip recorder 76 is provided in the control panel 70 to document the viscosity/flow measurement, the temperature of the sampled adhesive, and the various control signals that are sent out. Descriptive tags are added to the chart in order to show the samples origin if multiple tanks or sumps are used for sample testing.

If the monitoring system of FIG. 3 is constructed as a stand alone system, it can be integrated into an existing system comprising storage, mixing, or corrugator tanks and sumps. An alternative monitoring system includes an automatic starch system that has either a built-in or a stand alone personal computer coupled as part of the systems. The computer's power adds additional features above and beyond the features of the stand alone systems. Graphs can be generated to show the performance and the trends of the mixing system in order to document how the paste or adhesive reacts during daily operations. An alarm may be provided to set-up tolerance conditions for low or high measured viscosity/flow or temperature. With the computer power formulas can be automatically adjusted (such as to make the adhesive thicker/thinner, for example) based on the results of the monitoring.

The manufacture of adhesives begins in a mixing tank 90 where suitable means may be provided for converting raw materials into an adhesive. These means may be anything from manually dumping products into tank 90 to running various conveyors in order to bring in the products for adding starch, water, and other ingredients into the tank. Here in tank 90 is where the prior art usually measures the viscosity of the adhesive. The trouble has been that there is a major change as pure water, solid starch, or the like goes through its metamorphosis as it is converted into an adhesive. The prior art could not measure viscosity reliably as the adhesive in the mix tank can contain entrapped air, and due to environment it is difficult to supply a reliable measuring system According to the invention, only after the mixing step is completed is a sample suction valve 92 opened to draw a sample of the fully mixed paste or adhesive from mixer tank 90 responsive to an operation of pump 94. The sample is sent to the viscosity measuring testing tank 50. The drawing of the sample from the mixing tank 90 terminates when valve 92 closes under control of the signals sent from high and low sensors 54, 56 to the control panel 90.

If the viscometer 20 signal indicates an acceptable viscosity, the control panel causes the mixing tank to empty via pump 94, testing tank 50, valve 98, pump 100, valve 102, and one of the sample tank input or return valves 104–108. Preferably, each of the pumps 94, 100 is an air driven double diaphragm pump which is utilized to pump the paste or adhesive, especially during the testing process and during a switchover to another tank, mixer or sump. An air pump was selected due to its low shear operation and its ability to easily vary flow. While any of many suitable pumps may be used at 94 and 100, the system that was actually built used ARO one inch diaphragm pumps available from "The ARO Corporation" at One ARO Center, Bryan, Ohio 43506-0151. These pumps are driven by air from an air feed supply 109.

If the viscometer signal indicates a non-acceptable viscosity, the ratio of ingredients in the mixing tank are changed. If the controls have been added to a pre-existing system, almost any steps may be indicated from manually adding more starch and adjusting valves to running a conveyor or other automatic feed devices, as symbolized at auto feed 110. If the viscometer gives a signal indicating that there is a hopeless mix which cannot be corrected, valves 98, 111 are opened to dump the entire contents of the mixing tank 90 into a suitable drain 112.

If the mixture is acceptable, the control panel 70 selects and operates one of the valves 104–108 so that the adhesive is stored in one of the three or more storage tanks 113, 114, 115. Actually, any suitable number of storage tanks may be provided for any one of many reasons. The system provides two automatic valves (e.g. 104, 116) per storage tank or compartment. One valve 116 is used for a suction line extending from the tank 113 to the viscosity measurement testing tank 50. The other valve 104 is used for the return of the sample adhesive to the original storage tank after the viscosity reading is taken.

There may be a plurality of tanks when the adhesive is a type which may require aging. For example, tank 113 may be filling while the adhesive in tank 114 is aging and the adhesive in tank 115 is supplying a corrugator machine. When tank 115 is empty, the cycle advances and tank 113 ages, while tank 114 supplies the corrugator and tank 115 fills.

In another situation, the adhesive in tank 113 may be a type required for single face corrugated board, for example. The adhesive in tank 114 may be a type required for the second face board on a double faced corrugated board, for example. Likewise, any number of tanks may be provided for a number of other types of adhesive.

Periodically, the individual output or suction valves 116, 118, 120 may be selectively operated to draw a sample which is fed through pump 94 to the testing tank 50 where the viscometer 20 reads its characteristics. This reading monitors how the adhesive characteristics change with aging or when new adhesive is added to existing adhesive remaining in a tank. After the sample from the monitored one of the tanks 110–114 is read, the sample is returned to its storage tank via valve 98, pump 100, and valve 102, and one of the valves 104–108 selected by control panel 70 to the tank which supplied the sample that was tested.

The symbols at 98, 100, 111, 132–141 are manually operated valves. The symbols at 142–146 are pressure regulators. The pressure regulators which were used in the system that was actually built was a product of the Arrow Pneumatics Inc. at 500 Oakwood Road, Lake Zurich, Ill., 60047. When it is necessary to clean the sample tank or the viscometer, manual valve 141 is operated to supply flush water which washes out the testing tank 50 and is then drained via valves 98, 111.

The symbols at 92, 104–108, 116–120, 148, 150, 152 are various valves which are operated by solenoids controlled from the control panel 70.

The symbols 156, 158, 160 are lubricators which insure a proper operation of the air transfer pump.

In operation, a sample tank suction valve (e.g. 116) is opened. The air diaphragm transfer pump 94 turns on, pumping a sample of the adhesive to the testing tank 50 which fills until the fill level probe 62 indicates a correct level. When the fill probe 62 is satisfied, the viscometer 20 starts testing the adhesive in the testing tank 50 by allowing a small chamber 40 (FIG. 2) to be filled with adhesive and then dropping bushing and cap 42 onto the piston 44. A small clearance exists for the adhesive to be evacuated out of the bore in cap 42 as the piston fills it. A timing cycle is initiated at 24 upon the start of the cap's fall and ends upon the completion of the fall as limit switch 38 signals the start and end of the fall, a timer 24 times the fall cycle which is then converted into a "Stein-Hall Viscosity Reading." After the control panel 70 accepts the level, temperature, and level sensor signals, and the viscometer readings, the air diaphragm return pump 100 turns on and the sample return valve 104 opens. Thus, the tested sample of adhesive returns to its origin via a sample recirculation loop.

Those who are skilled in the art will readily perceive how to modify the invention. Therefore, the appended claims are to be construed to cover all equivalent structures which fall within the true scope and spirit of the invention.

The claimed invention is:

1. A control system for supplying adhesive or paste to corrugators that make corrugated cardboard, said system comprising at least one mixing tank for mixing ingredients to make adhesive or paste, a viscometer, a testing tank containing said viscometer, at least one storage tank for storing adhesive or paste, and an adhesive or paste transfer system for transferring adhesive or paste from said mixing tank to said testing tank before a transfer to said storage tank, a viscosity test being conducted in said testing tank before said adhesive or paste is transferred to said storage tank, and central control means for selectively controlling said transfer of said adhesive or paste in response to at least test result signals from said viscometer.

2. The system of claim 1 further comprising a temperature sensor in said testing tank, and means jointly responsive to said signals from said viscometer and said temperature sensor for automatically adjusting operations of said mixing tank when needed for correcting said adhesive or paste.

3. The system of claim 1 wherein there are a plurality of said storage tanks, each of said storage tanks and said mixing tank having individually associated output valves for selectively delivering said adhesive or paste from the individually associated tank to said testing tank, and means for cyclically and successively operating said output valves to couple each of said tanks one at a time to said testing tank.

4. The system of claim 3 wherein each of said storage tanks further comprises individually associated input valves for selectively returning adhesive or paste from said testing tank to the individually associated storage tank, and means for cyclically and successively operating said output and input valves to transfer samples of adhesive or paste from said storage tanks one at a time to said testing tank and to return said samples of adhesive or paste into the same storage tank from which they were taken.

5. The system of claim 1 wherein said viscometer comprises a bushing and cap having a bore therein, said bushing and cap being movable between a lower and a raised position, a stationary piston which almost fills said bore when said bushing and cap is in said lower position and which enables said bore to fill with adhesive or paste when said bushing and cap is in a raised position, there being a small clearance space between a wall of said bore and said piston, timing means for measuring a period of time required for said bushing and cap to free fall from said raised position to said lower position, as said adhesive or paste exits said bore, and means responsive to said timing means for adjusting an operation of said system.

6. In an adhesive or paste making system for use in a corrugated cardboard production, the combination comprising:

a mixer tank for converting raw materials into adhesive or paste;

a plurality of storage tanks for individually storing said adhesive or paste;

a separate testing tank located between said mixer tank and said storage tanks for monitoring viscosity of said adhesive or paste in said mixer tank and in said individual storage tanks;

a network of pipes and valves for selectively drawing a sample of adhesive or paste from either a selected one of said storage tanks or said mixing tank, forwarding said sample of adhesive or paste to said testing tank, conducting a test on said sample, and returning said sample to said selected one of said storage tanks;

means in said testing tank for measuring the viscosity of the drawn sample during said test and for giving a signal indicating the viscosity measured while said drawn sample is in said testing tank, and control means responsive to said viscosity signal for controlling the operation of said adhesive or paste making system by controlling the feeding of ingredients into the system.

7. The system of claim 6 and means responsive to said control means for selectively operating said valves for routing said drawn sample through said network of pipes.

8. The system of claim 6 and means in said testing tank for measuring and given a temperature signal indicating the temperature of the adhesive or paste in said testing tank, and wherein said control means operates in response jointly to said viscosity signal and said temperature signal.

9. The system of claim 6 and at least one low shear air driven double diaphragm pump for moving said adhesive or paste through said network of pipes.

10. The system of claim 6 wherein said means for measuring the viscosity of the drawn sample comprises a bushing and cap which is first moved to a raised position for drawings in said adhesive or paste, timing means for measuring a period of time required for said bushing and cap to free fall from said raised position to a lower position where said adhesive or paste is expelled from said bushing and cap, and means responsive to said timing means for controlling said operation of said system.

11. A system for making adhesive or paste for a corrugator, said system comprising first means for converting raw materials into said adhesive or paste, means for storing said adhesive or paste, test means separate from said converting means and from said storing means for testing viscosity and temperature of said adhesive or paste, said operation of said converting means occurring in response to said testing means and before said storing of said adhesive or paste in said storing means, means for also transferring individual samples of said converted adhesive or paste and said stored adhesive or paste to said testing means where a viscosity test is conducted, transport means for transporting samples from said converting means to said test means and from said storing means to said test means and for returning said samples to said storing means after testing in said test means, control means responsive to said test means for cyclically operating said transport means to take samples of said adhesive or paste to and from said testing means, and means also responsive to said control means for controlling the feeding of said raw materials into the system.

12. The system of claim 10 wherein there are a plurality of said storing means, and said control means sequentially takes samples from each of said storing means and after testing by said testing means returns said samples to the storing means from which it was taken, whereby the adhesive or paste in each of said storage means may have characteristics which are different from the characteristics of paste in other of said storage means.

13. The system of claim 11 and means responsive to said control means for automatically controlling said converting means to bring said adhesive or paste into a desired characteristic.

14. The system of claim 12 wherein said testing means comprises a bushing and a cap is in a raised position which takes in said adhesive, timing means for measuring a period of time required for said bushing and cap to free fall from said raised position to said lower position expelling said adhesive or paste in the fall, and means responsive to said timing means for controlling an operation of said system.

15. The system of claim 12 and means for generating graphs documenting testing results for said adhesive or paste.

16. The system of claim 10 wherein said test means comprises a testing tank for receiving said adhesive or paste, a pair of RF detecting test probes for sensing a working level and a high level of said adhesive or paste in said tank by detecting an RF signal, and means responsive to said probe being submerged in said adhesive or paste for precluding said detection of said RF signal by said submerged probes, and means responsive to said test probes for terminating a filling of said testing tank and conducting said viscosity testing.

\* \* \* \* \*